United States Patent
Gottwik et al.

(10) Patent No.: US 9,783,459 B2
(45) Date of Patent: Oct. 10, 2017

(54) ZIRCONIUM OXIDE-BASED COMPOSITE MATERIAL

(71) Applicant: CeramTec GmbH, Plochingen (DE)

(72) Inventors: Lukas Gottwik, Heiningen (DE); Meinhard Kuntz, Esslingen (DE); Alessandro Alan Porporati, Esslingen (DE); Juliane Ehrlich, Stuttgart (DE); Andreas Morhardt, Esslingen (DE); Kilian Friederich, Plochingen (DE)

(73) Assignee: CeramTec GmbH, Plochingen (DE)

( * ) Notice: Subject to any disclaimer, the term of this patent is extended or adjusted under 35 U.S.C. 154(b) by 0 days.

(21) Appl. No.: 14/422,541

(22) PCT Filed: Aug. 20, 2013

(86) PCT No.: PCT/EP2013/067281
§ 371 (c)(1),
(2) Date: Feb. 19, 2015

(87) PCT Pub. No.: WO2014/029757
PCT Pub. Date: Feb. 27, 2014

(65) Prior Publication Data
US 2015/0175485 A1    Jun. 25, 2015

(30) Foreign Application Priority Data

Aug. 20, 2012  (DE) .................. 10 2012 214 749
Sep. 4, 2012   (DE) .................. 10 2012 215 658

(51) Int. Cl.
*C04B 35/119*  (2006.01)
*A61C 13/083*  (2006.01)
(Continued)

(52) U.S. Cl.
CPC ........ *C04B 35/4885* (2013.01); *A61C 8/0012* (2013.01); *A61C 13/08* (2013.01);
(Continued)

(58) Field of Classification Search
CPC .................... C04B 35/488; C04B 35/4885
See application file for complete search history.

(56) References Cited

U.S. PATENT DOCUMENTS 4,316,964 A * 2/1982 Lange ............... C04B 35/119
                                               501/105
4,820,666 A * 4/1989 Hirano ............. C04B 35/119
                                               501/104
(Continued)

FOREIGN PATENT DOCUMENTS

DE    40 20 893 A1    1/1991
DE   195 40 452 A1    3/1997
(Continued)

OTHER PUBLICATIONS

Shen, et al. "Dense Hydroxyapatite-Zirconia Ceramic Composites with High Strength for Biological Applications", Adv. Mater., 13, No. 3, (2001), pp. 214-216.

*Primary Examiner* — Karl Group
(74) *Attorney, Agent, or Firm* — Norton Rose Fulbright US LLP

(57) ABSTRACT

A ceramic composite material and a method for producing same. The ceramic composite material has a ceramic matrix comprising zirconium oxide and at least one secondary phase dispersed therein. The matrix is composed of zirconium oxide as at least 51 vol.-% of composite material, and the secondary phase is in a proportion of 1 to 49 vol.-% of composite material, wherein 90 to 99% of the zirconium oxide is present in the tetragonal phase based on the total zirconium oxide portion. The tetragonal phase of the zirconium oxide is stabilized by at least one member selected from the group consisting of chemical stabilization and mechanical stabilization. The ceramic composite is damage-tolerant.

26 Claims, 4 Drawing Sheets

(51) Int. Cl.

| | |
|---|---|
| *A61L 27/10* | (2006.01) |
| *C04B 35/488* | (2006.01) |
| *A61L 27/42* | (2006.01) |
| *A61K 6/02* | (2006.01) |
| *C04B 35/626* | (2006.01) |
| *C04B 35/645* | (2006.01) |
| *A61L 27/12* | (2006.01) |
| *A61L 27/50* | (2006.01) |
| *A61C 8/00* | (2006.01) |
| *A61C 13/08* | (2006.01) |
| *C04B 41/91* | (2006.01) |
| *A61F 2/30* | (2006.01) |

(52) U.S. Cl.
CPC .............. *A61K 6/024* (2013.01); *A61K 6/025* (2013.01); *A61K 6/0205* (2013.01); *A61K 6/0255* (2013.01); *A61L 27/10* (2013.01); *A61L 27/105* (2013.01); *A61L 27/12* (2013.01); *A61L 27/427* (2013.01); *A61L 27/50* (2013.01); *C04B 35/488* (2013.01); *C04B 35/62655* (2013.01); *C04B 35/6455* (2013.01); *C04B 41/91* (2013.01); *A61F 2/30965* (2013.01); *A61F 2002/30952* (2013.01); *A61F 2002/30968* (2013.01); *A61F 2002/30986* (2013.01); *A61F 2310/00197* (2013.01); *A61F 2310/00203* (2013.01); *A61F 2310/00215* (2013.01); *A61F 2310/00239* (2013.01); *A61F 2310/00293* (2013.01); *A61L 2430/12* (2013.01); *A61L 2430/38* (2013.01); *C04B 2235/32* (2013.01); *C04B 2235/3203* (2013.01); *C04B 2235/3206* (2013.01); *C04B 2235/3208* (2013.01); *C04B 2235/3212* (2013.01); *C04B 2235/3213* (2013.01); *C04B 2235/3218* (2013.01); *C04B 2235/3222* (2013.01); *C04B 2235/3224* (2013.01); *C04B 2235/3225* (2013.01); *C04B 2235/3227* (2013.01); *C04B 2235/3229* (2013.01); *C04B 2235/3232* (2013.01); *C04B 2235/3239* (2013.01); *C04B 2235/3241* (2013.01); *C04B 2235/3246* (2013.01); *C04B 2235/3248* (2013.01); *C04B 2235/3272* (2013.01); *C04B 2235/349* (2013.01); *C04B 2235/3418* (2013.01); *C04B 2235/3427* (2013.01); *C04B 2235/3463* (2013.01); *C04B 2235/3472* (2013.01); *C04B 2235/442* (2013.01); *C04B 2235/445* (2013.01); *C04B 2235/661* (2013.01); *C04B 2235/72* (2013.01); *C04B 2235/765* (2013.01); *C04B 2235/785* (2013.01); *C04B 2235/786* (2013.01); *C04B 2235/80* (2013.01); *C04B 2235/96* (2013.01); *C04B 2235/9669* (2013.01)

(56) References Cited

U.S. PATENT DOCUMENTS

| | | | |
|---|---|---|---|
| 5,232,878 | A | 8/1993 | Kasuga et al. |
| 5,525,560 | A * | 6/1996 | Yamazaki ............. C04B 35/488 501/103 |
| 5,863,850 | A | 1/1999 | Nawa et al. |
| 7,012,036 | B2 * | 3/2006 | Nawa .................. C04B 35/4885 501/105 |
| 7,056,851 | B2 * | 6/2006 | Nawa .................... C04B 35/119 501/105 |
| 7,148,167 | B2 * | 12/2006 | Shikata ................ C04B 35/119 501/104 |
| 7,928,028 | B2 * | 4/2011 | Nawa .................... C04B 35/119 501/105 |
| 8,093,168 | B2 * | 1/2012 | Nawa .................... C04B 35/119 501/105 |
| 8,889,576 | B2 | 11/2014 | Hoeland et al. |
| 2007/0049484 | A1 | 3/2007 | Kear et al. |
| 2009/0292366 | A1 | 11/2009 | Burger et al. |
| 2009/0317767 | A1 | 12/2009 | Burger et al. |
| 2012/0082849 | A1 * | 4/2012 | Nonnet ................. C04B 35/119 428/402 |
| 2012/0252656 | A1 | 10/2012 | Kuntz et al. |
| 2012/0295113 | A1 * | 11/2012 | Kurizoe ................ B82Y 30/00 428/402 |
| 2015/0035210 | A1 | 2/2015 | Hoeland et al. |

FOREIGN PATENT DOCUMENTS

| | | |
|---|---|---|
| DE | 10 2008 042 015 A1 | 3/2010 |
| EP | 2 377 506 A1 | 10/2011 |
| WO | 2008/040813 A1 | 4/2008 |
| WO | 2011/083023 A1 | 7/2012 |
| WO | 2013/004361 A2 | 1/2013 |

* cited by examiner

ZIRCONIUM OXIDE-BASED COMPOSITE MATERIAL

This application is a §371 of International Application No. PCT/EP2013/067281 filed Aug. 20, 2013, and claims priority from German Patent Application Nos. 10 2012 214 749.7 filed Aug. 20, 2012 and 10 2012 215 658.5 filed Sep. 4, 2012.

FIELD OF THE INVENTION

The invention relates to a ceramic composite material and its production and use. In particular, the invention relates to a zirconium oxide-based composite material which is a homogeneous, multiphase, biocompatible, polycrystalline ceramic.

BACKGROUND OF THE INVENTION

Zirconium oxide-based composite material may be used in the dental sector in the production of bridges and crowns, for example in the production of dental implants, in the production of medical components such as spinal implants, but also in general in areas in which a technical ceramic with damage-free hard machinability is required, for example in machining operations such as cutting, milling, and drilling.

Ceramic materials have advantages over conventional metallic materials in the dental market due to their chemical resistance, mechanical and physical properties, and optical properties, which provide excellent esthetics.

The general trend in dental ceramics is toward "full ceramic systems." However, at the present time ceramics are still frequently applied as veneers on metallic frameworks. Dental ceramics may be classified based on their production method and their crystalline phase.

Metal-ceramic systems have been in existence since 1960. A veneer ceramic is applied to a metal framework in order to obtain an esthetically acceptable restoration which resembles the natural tooth. Typical veneer materials are composed of feldspathic glasses, and are usually based on leucite crystal. The addition of leucite crystals ($KAlSi_2O_6$) into the feldspathic glass structure results in optimal properties with regard to the coefficients of thermal expansion of the framework and the veneer. Leucite crystals are formed by incongruent melting of natural feldspar at temperatures between 1150 and 1530° C. The coefficient of thermal expansion may be controlled in a targeted manner and adapted to the metallic framework by varying the leucite crystal content. The typical leucite crystal content in feldspathic glass is commonly between 15 and 25 vol.-%. The coefficient of thermal expansion is thus lower than that of the metal, and the applied veneer is placed under pressure. In the classical process, veneer ceramics are sintered under vacuum to reduce the porosity in the final product. On account of the glass phase, the mechanical properties of the leucite crystal-based glasses (also referred to as dental porcelain) are the lowest of all ceramic materials used in dentistry. As of 2005, 50% of all dental restorations were produced using metal-ceramic systems.

Full ceramic systems are free of metal, and have been available for 30 years. The process technology is undergoing continuous development (hot pressing, slip casting, CAD/CAM machining, for example). The main difference from the metal-ceramic systems is a much higher proportion of the crystalline phase, which may be between 35 and 100 vol.-%. Although the mechanical properties are improved, the opacity is increased, which is disadvantageous with regard to the required esthetics.

There are a number of factors that have an influence on the longevity of the full ceramic systems, such as the oral environment, fluctuating pH values from acidic to basic, cyclical load, and extreme load peaks during chewing. Full ceramic systems having higher proportions of the glass phase frequently exhibit stress corrosion cracking as the cause of failure. Due to the hydrothermal aging of Y-TZP ceramics (100 vol.-% crystalline phase, Y-stabilized tetragonal zirconium oxide) at low temperatures, testing according to standards is required in which the longevity in the human environment and under cyclical load is to be assessed.

Full ceramic systems are classified primarily based on the production method (hot pressing, dry pressing and sintering, slip casting, CAD/CAM machining, for example). In hot pressing, leucite crystal-based glasses having a crystalline phase proportion between 35 and 45 vol.-% are initially used. The mechanical properties are higher than those of the leucite crystal-based glasses of the metal-ceramic systems by a factor of 2. Repeated heating may facilitate the leucite crystallization and may result in greater strength.

A novel glass ceramic is presently used for the hot pressing. The material is composed of a lithium disilicate-based glass having a crystalline phase proportion of 65 vol.-%. X-ray analyses have identified lithium disilicate ($Li_2Si_2O_5$) in addition to further crystal phases such as lithium metasilicate ($Li_2SiO_3$) and cristobalite ($SiO_2$). The mechanical properties are once again higher than those of the leucite crystal-based glasses by a factor of 2.

The dry pressing and sintering of full ceramic systems has been used since the early 1990s. The production is carried out with computer assistance, and takes into account the sintering shrinkage of the compacted blank during sintering. Ceramics based on aluminum oxide and zirconium oxide (100 vol.-% crystalline phase proportion) are used as the framework material, upon which a veneer made of glass ceramic is additionally applied. Aluminum oxide ceramics are characterized by a flexural strength of approximately 600 MPa and excellent in vivo behavior.

Slip casting has been used since the 1990s. In the process, a porous green body is produced from crystalline phases by means of slip casting, subsequently sintered, and infiltrated with a lanthanum-based glass.

The following glass ceramics are available on the dental market: aluminum oxide ($Al_2O_3$), spinel ($MgAl_2O_4$), and 12Ce-TZP/$Al_2O_3$ composite. The glass-infiltrated aluminum oxide has mechanical properties comparable to those of lithium disilicate-based glass ceramic, but has a minimally higher opacity. The glass-infiltrated spinel has much higher translucence and comparable mechanical properties compared to lithium disilicate-based glass ceramic. The glass-infiltrated zirconium oxide/aluminum oxide composite exhibits the highest strength and fracture toughness of all slip-cast dental ceramics.

The computer-controlled CAD/CAM machining of ceramic blocks and blanks has been carried out since the early 1970s, and was introduced by Duret. At that time, the machining was performed on dense-sintered blanks. Presently, operations are carried out primarily using pre-sintered blanks.

Glass ceramic is suitable for CAD/CAM machining in the dense-sintered state due to its very good machinability. Typical mica crystal-based glasses were formerly used on account of the ideal machinability. At the present time, feldspathic glasses containing sanidine, leucite, or lithium disilicate crystals are used. However, the CAD/CAM machining on dense-sintered glass ceramics shows significant tool wear. Surface defects may adversely affect the in vivo behavior.

In general, glass ceramics have very good machinability. Microcracks develop along the phase boundaries due to differing coefficients of thermal expansion of the crystal and the glass matrix during cooling. In addition, the crystalline phases have very good cleavability along the longitudinal orientation (primarily mica along the crystallographic (001) plane). The crystal phases should have no preferred orientation; i.e., they should be isotropically distributed in the glass structure. A crack introduced by a tool runs along the cleavage plane or also along the phase boundary between the crystal and the glass matrix. As a result, the crack is continuously deflected during the machining, and only small areas of the surface are broken out from the workpiece.

Since 2001, CAD-CAM machining has been carried out on pre-sintered zirconium oxide blanks. The machining is easier and quicker, and shows lower tool wear than when dense-sintered blocks had to be machined. However, the finished workpieces must subsequently be dense-sintered. Fluctuations in the sintering shrinkage, accompanied by dimensional deviations and touch-up operations performed manually by dental technicians, result in an increased risk of damage to the zirconium oxide.

Thus far, zirconium oxide as the framework material has the best mechanical properties. However, due to phase transformation of the tetragonal zirconium oxide phase, cracks frequently occur at the interface between the framework and the veneer on account of the additional required veneer ceramic. Several previously published 3-year and 5-year in vivo studies have already been conducted quite some time ago.

The studies concluded that there is an excellent success rate, but with a low survival rate with complications such as incidence of dental caries or chipping of the veneer. The current development trend is clearly toward zirconium oxide/aluminum oxide composite materials, with the objectives of improving the hydrothermal aging resistance and the mechanical properties.

OBJECT AND SUMMARY OF THE INVENTION

The object of the invention is to avoid the disadvantages of the prior art, and in particular to provide a ceramic whose mechanical properties allow damage-free hard machining and/or which have good hydrothermal aging resistance. In addition, the aim is for the ceramic to be producible and machinable using common processes. This object is achieved by a composite material having a ceramic matrix composed of zirconium oxide and at least one secondary phase dispersed therein, characterized in that the matrix composed of zirconium oxide has a proportion of at least 51 vol.-% of composite material, and that the secondary phase has a proportion of 1 to 49 vol.-% of composite material, wherein preferably 90 to 99%, particularly preferably 95 to 99%, based on the total zirconium oxide portion, of the zirconium oxide is present in the tetragonal phase, and the tetragonal phase of the zirconium oxide is chemically and/or mechanically stabilized and an associated method.

DETAILED DESCRIPTION

Figure 1:
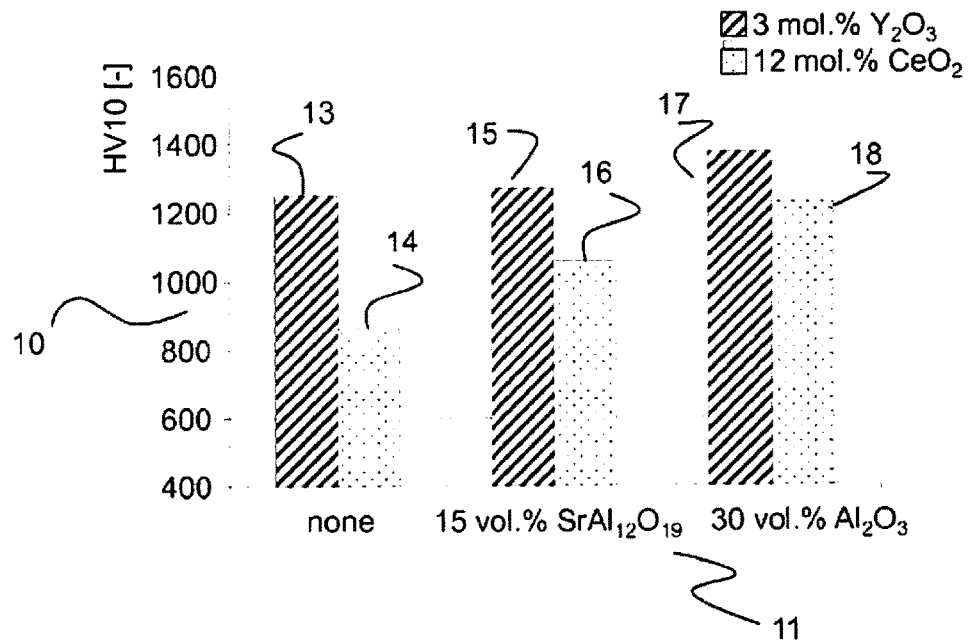
FIG. 1 shows the results of a test series with and without dispersoids according to the invention, in each case with different chemical stabilizers.

The advantages of the novel material according to the invention over the prior art are quantitatively determined based on the improved "damage tolerance." Damage tolerance is a mechanical characteristic value which describes the resistance of a material to an externally applied damage. The damage may occur in practice, for example, due to grinding using diamond tools.

For measuring the damage tolerance in the laboratory, the test piece is subjected to damage using a diamond tip (Vickers) under a defined stress force. Cracks form in the area of the hardness indentation, so that the test piece experiences weakening at this location. The weakening is quantitatively determined by measuring the residual breaking stress, i.e., residual strength, at this location. The higher the residual strength after a defined weakening, the higher the damage tolerance of the material.

For the detailed description of the damage tolerance, a series of test pieces is subjected to damage, using different stress forces. This results in a characteristic curve for the material (residual strength versus stress force). Improved damage tolerance of a material with respect to the prior art is demonstrated by comparing these characteristic curves; see FIGS. 7 and 8.

The invention relates to the production and use of a zirconium oxide-based composite material, in particular for damage-free hard machining in the dense-sintered state. The production of the composite material according to the invention is carried out using conventional ceramic technology which is known per se. The important process steps are, for example:

a) Placing powder mixture according to the predefined composition into water, optionally using liquefiers to avoid sedimentation
b) Homogenization in a dissolver (high-speed agitator)
c) Grinding in an agitator ball mill, thus increasing the specific surface of the powder mixture (comminution and homogenization)
d) Optionally adding organic binders
e) Spray drying, resulting in a pourable granulate having defined properties f) Moistening the granulate with water and optionally further pressing aids
g) Axial pressing of blocks
h) Machine cutting of blocks in the green or pre-sintered state, thus largely imparting the final contour, taking the sintering shrinkage into account
i) Sintering (This may also take place in a 3-step sintering process: prefiring to a theoretical density of approximately 97%. The remaining residual pores are closed from the outside. Hot isostatic pressing (HIP) under high temperature and high gas pressure, resulting in virtually complete final compaction. So-called white burning, thus compensating for the imbalance of oxygen ions, produced during the hot isostatic pressing, in the ceramic.)
j) Hard machining by grinding and polishing with a diamond tool.

The composite material according to the invention may be used, for example, for producing sintered molded bodies, for producing artificial dental prostheses and dental restorations such as bridges, crowns, inlays, and onlays, and for producing dental root pins, implants, and abutments. The application in the area of implant technology is preferred. The application in the spinal area as a spacer or cage is particularly preferred.

The zirconium oxide-based composite material contains zirconium oxide as the ceramic matrix, and at least one secondary phase or dispersoid and optionally further additives dispersed therein. The composite material includes as the first phase a zirconium oxide proportion of at least 51 vol.-% and a secondary phase having a proportion of 1 to 49 vol.-%, and optionally one or more inorganic additives. The predominant portion, preferably 90 to 99%, particularly preferably 95 to 99%, based on the total zirconium oxide portion, of the zirconium oxide is present in the tetragonal phase, wherein the stabilization of the tetragonal phase of the zirconium oxide sometimes takes place not only chemically but also mechanically. The terms "secondary phase" and "dispersoid" are used synonymously within the scope of this text.

The mechanical stabilization of the zirconium oxide, in addition to the chemical stabilization, which is present in the tetragonal phase, advantageously allows the content of chemical stabilizers to be reduced compared to the prior art.

The mechanical stabilization of the zirconium oxide in the tetragonal phase is known from zirconia toughened alumina (ZTA) composite materials. In that context, it has been assumed that the mechanical stabilization is influenced on the one hand by the grain size of the zirconium oxide. In aluminum oxide composite materials, this grain size should not be greater than 0.5 μm, measured according to the linear intercept method. On the other hand, it has been assumed that the embedding of the individual zirconium oxide particles in the aluminum oxide matrix has a significant portion of the mechanical stabilization, wherein minimum contents of aluminum oxide of 65 vol.-%, preferably higher contents, have been considered necessary.

With the present invention, it has been possible to demonstrate that such mechanical stabilization of the zirconium oxide functions not only when zirconium oxide is incorporated into aluminum oxide as the dispersoid phase, but also in a ceramic which is composed substantially of zirconium oxide. The addition according to the invention of the secondary phases/dispersoids compensates for the strain which occurs during the transformation of the tetragonal crystal structure into the monoclinic crystal structure of the zirconium oxide, in that micromotions/microshears on the crystallite level are possible in an otherwise comparatively rigid ceramic structure without macroscopic cracks necessarily arising.

Furthermore, mechanical stabilization is also understood to mean that the tetragonal crystal phase of the zirconium oxide is stabilized by mechanical stresses in the overall structure. Different coefficients of thermal expansion of $ZrO_2$ and of the secondary phase during cooling after the sintering process may result in such stresses.

The mechanical stabilization is advantageous in particular in that lower proportions of compounds used for the chemical stabilization are thus necessary. The chemical stabilization is based on the partial substitution of zirconium oxide ions with cations which produce oxygen vacancies in the crystal lattice, and which thus have a smaller "space requirement" However, the oxygen vacancies in the lattice may be points of attack for hydrothermal aging. Mechanical stabilization, which at the same time at least reduces the need for chemical stabilization, thus results in improved resistance of the composite material to hydrothermal aging.

According to one preferred embodiment of the invention, the zirconium oxide matrix has an average grain size of 0.1 to 2.0 μm, particularly preferably 0.5 to 2.0 μm on average.

According to one refinement of the invention, the proportion of chemical stabilizers in the composite material according to the invention for $Y_2O_3$ is ≤3 mol-%, preferably ≤2.5 mol-%, for $CeO_2$ is ≤12 mol-%, for $Gd_2O_3$ is ≤3 mol-%, for $Sm_2O_3$ is ≤3 mol-%, and for $Er_2O_3$ is ≤3 mol-%, the proportion in each case relative to the zirconium oxide content. The chemical stabilizers in the composite material according to the invention include one or more of the mentioned additives, with $Y_2O_3$ being preferred. The total content of chemical stabilizers is advantageously <12 mol-% relative to the $ZrO_2$ content.

According to one embodiment, the zirconium oxide and the dispersoid may contain soluble substituents. Soluble substituents may be Cr, Fe, Mg, Ca, Ti, Y, Ce, lanthanides, and/or V, for example. These substituents may function on the one hand as color additives, and on the other hand as sintering aids. The substituents are generally added as oxides.

The particle sizes of the secondary phase or dispersoids are preferably not much greater than the grain sizes of the zirconium oxide matrix. The former are preferably 0.2 to 2.0 μm, particularly preferably 0.2 to 0.5 μm. The volume proportion of the secondary phase or dispersoids is much lower than the proportion of the zirconium oxide, and is up to 49 vol.-%, preferably 1 to 10 vol.-%, particularly preferably 4 to 6 vol.-%, of the total volume. The secondary phase is chemically stable, and does not go into solution in the zirconium oxide during production of the composite material due to sintering at high temperatures.

The following compounds may be used as the secondary phase or dispersoids: Strontium aluminate ($SrAl_{12}O_{19}$), lanthanum aluminate ($LaAl_{11}O_{18}$), hydroxyapatite ($Ca_{10}(PO_4)_6(OH)_2$), fluorapatite ($Ca_{10}(PO_4)_6F_2$), tricalcium phosphate ($Ca_3(PO_4)_2$), spinel ($MgAl_2O_4$), aluminum oxide ($Al_2O_3$), yttrium aluminum garnet ($Y_3Al_5O_{12}$), mullite ($Al_6Si_2O_{13}$), zircon ($ZrSiO_4$), quartz ($SiO_2$), talc ($Mg_3Si_4O_{10}(OH)_2$), kaolinite ($Al_2Si_2O_5(OH)_4$), pyrophyllite ($Al_2Si_4O_{10}(OH)_2$), potassium feldspar ($KAlSi_3O_8$), leucite ($KAlSi_2O_6$), and lithium metasilicate ($Li_2SiO_3$). Strontium aluminate, lanthanum aluminate, hydroxyapatite, fluorapatite, spinel, aluminum oxide, and zircon are preferred, and lanthanum aluminate, fluorapatite, spinel, and aluminum oxide are particularly preferred.

The secondary phase or dispersoids may allow inelastic microdeformations on the microscopic level, and due to their crystal structure may allow shear deformations on the microscopic level.

According to one particularly preferred embodiment of the invention, the secondary phase is not formed during the sintering, but, rather, is part of the starting substances used for producing the ceramic.

The breaking strength of the composite material is preferably 800 MPa.

It has surprisingly been shown that the secondary phase or dispersoids may greatly reduce the hardness of the composite material. Likewise, it has surprisingly been shown that the type of chemical stabilizer has a great influence on the hardness of the composite material.

Furthermore, it has surprisingly been shown that the fracture toughness, the hardness, and the damage tolerance of the composite material are influenced by the type and the quantity of the secondary phase or dispersoids, and by the type of chemical stabilizer.

The present invention is explained below with reference to test series, without being limited thereto:

Test Series 1: Hardness as a Function of the Chemical Stabilizer

FIG. 1 shows the results of a test series with and without dispersoids according to the invention, and in each case with different chemical stabilizers. The quantity and type of the dispersoid phase used, namely, zirconium oxide containing no dispersoids with $Y_2O_3$ stabilization 13 or $CeO_2$ stabilization 14, zirconium oxide containing 15 vol.-% strontium hexaaluminate dispersoids and $Y_2O_3$ stabilization 15 or $CeO_2$ stabilization 16, and zirconium oxide containing 30 vol.-% $Al_2O_3$ dispersoids and $Y_2O_3$ stabilization 17 or $CeO_2$ stabilization 18, are represented on the x axis 11, and the Vickers hardness HV 10 is represented on the y axis 10.

The chemical stabilizers yttrium oxide ($Y_2O_3$) and cerium oxide ($CeO_2$) were tested. It has surprisingly been shown that all variants with Ce stabilization 14, 16, 18 have much lower hardness values compared to variants with Y stabilization 13, 15, 17. The hardness was determined by Vickers indentation (HV10) with a force of 98.07 N.

Pure Ce-stabilized zirconium oxide has the lowest hardness at 800 (HV10). With regard to the application according to the invention in the dental field, lower hardnesses are desired. In the regions of the molar teeth, an artificial dental prosthesis made of frequently used Y-TZP may strike against a natural tooth. The hardness of Y-TZP is approximately 1250 (HV10). The natural tooth or the enamel has a much lower hardness of approximately 400 (HV10) due to the incorporated hydroxyapatite crystals. For stress-related grinding of the teeth (bruxism), for example, this difference in hardness may result in significant abrasion of the natural tooth. For this reason, lower hardnesses of the composite material according to the invention are expedient. In addition, a lower hardness of the composite material could result in damage-free hard machining (for example, during grinding-in of the artificial tooth in an articulator).

Test Series 2: Hardness as a Function of the Type of Dispersoid Phase

Figure 2:
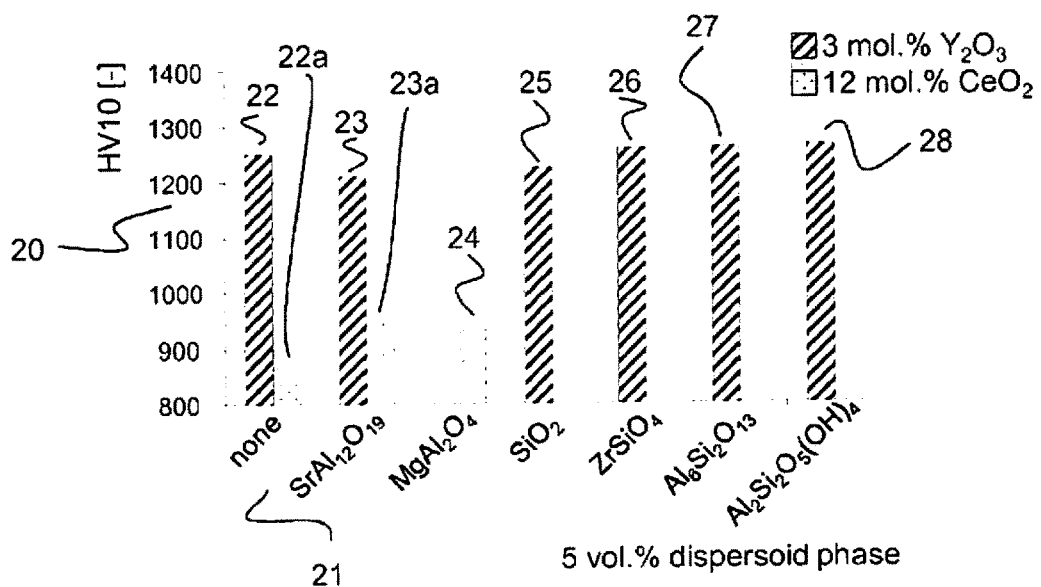
FIG. 2 shows a test series with different dispersoids in the composite material according to the invention.

FIG. 2 shows a test series with different dispersoids in the composite material according to the invention. In the test series, only variants having the same proportion (5 vol.-%) of the dispersoid phase in the composite material were compared to one another. The Vickers hardness HV 10 is provided on the y axis 20. The x axis 21 shows zirconium oxide in each case with 5 vol.-% dispersoids ($SrAl_{12}O_{19}$ 23, 23a, $MgAl_2O_4$ 24, 24a, $SiO_2$ 25, $ZrSiO_4$ 26, $Al_6Si_2O_{13}$ 27, $Al_2Si_2O_5(OH)_4$ 28), and without dispersoids 22, 22a for comparison. Variants with $Y_2O_3$ stabilization 22, 23, 24, 25, 26, 27 and 28 were tested for all compositions, and in addition, variants with $CeO_2$ stabilization 22a, 23a were tested for the zirconium oxide composite materials containing strontium hexaaluminate and spinel as dispersoids.

It has surprisingly been shown that the hardness may be influenced by adding dispersoids. It has likewise been shown that the degree of influence is a function of the composition of the dispersoid phase.

Test Series 3: Hardness as a Function of the Content of the Dispersoid Phase

Figure 3:
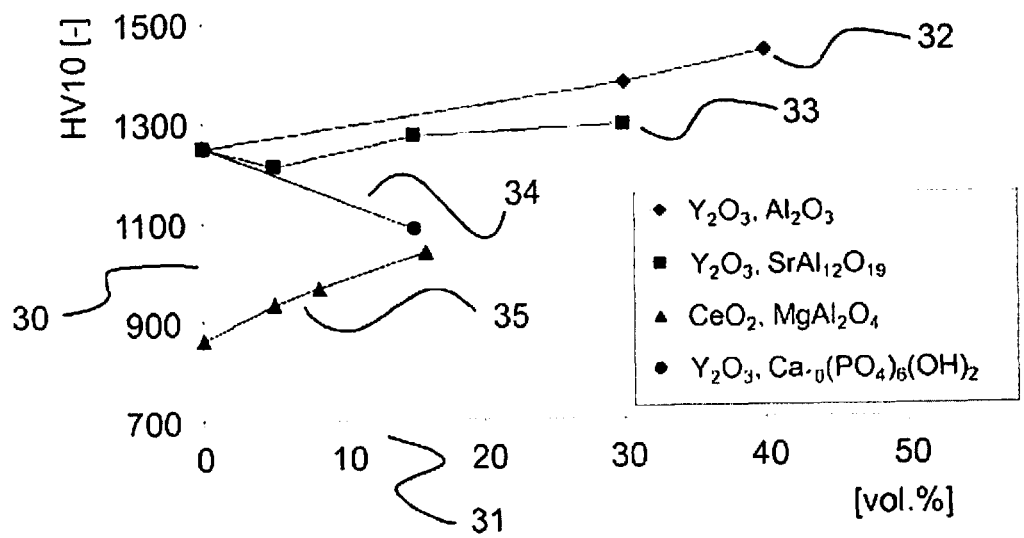
FIG. 3 shows a plurality of test series with dispersoids according to the invention and different contents (vol.-%) of dispersoid phases (x axis 31).

FIG. 3 shows a plurality of test series with dispersoids according to the invention and different contents (vol.-%) of the dispersoid phases (x axis 31). Aluminum oxide ($Al_2O_3$) 32, hydroxyapatite ($Ca_{10}(PO_4)_6(OH)_2$) 34, and strontium hexaaluminate ($SrAl_{12}O_{19}$) 33 in Y-stabilized zirconium oxide and spinel ($MgAl_2O_4$) 35 were tested in Ce-stabilized zirconium oxide.

It has surprisingly turned out that the Vickers hardness, plotted on the y axis 30, may be greatly influenced by the content of the dispersoid phase. The hardness of the composite material customarily results from the percentage mix of the individual hardnesses of the components involved. In the test series it has surprisingly been shown that this mixture rule does not always apply. The hardness may be reduced from approximately 1250 to approximately 1050 (HV10) by introducing 15 vol.-% hydroxyapatite 34 into Y-stabilized zirconium oxide. The hardness of Y-stabilized zirconium oxide may be reduced from 1250 to 1210 (HV10) by introducing 5 vol.-% strontium aluminate 33.

Test Series 4: Fracture Toughness as a Function of the Chemical Stabilizer

Figure 4:
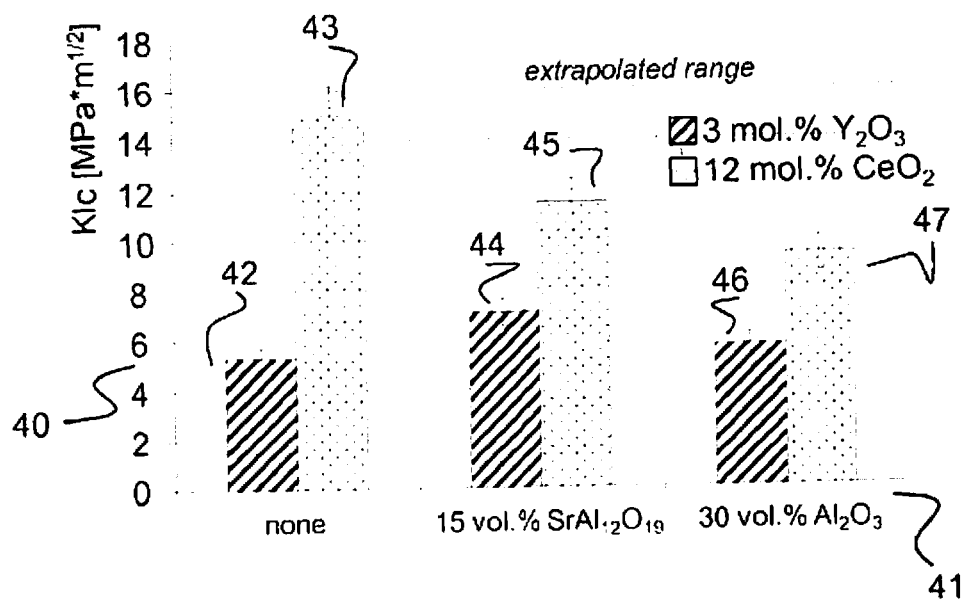
FIG. 4 shows a test series which illustrates the influence of the chemical stabilizer on pure zirconium oxide material and on the composite material according to the invention.

FIG. 4 shows a test series which illustrates the influence of the chemical stabilizer on the pure zirconium oxide material and the composite material according to the invention. The material containing the particular dispersoid phase is indicated on the x axis, namely, pure zirconium oxide 42, 43, zirconium oxide containing 25 vol.-% strontium hexaaluminate as the dispersoid phase 44, 45, and zirconium oxide containing 30 vol.-% $Al_2O_3$ as the dispersoid phase 46, 47, in each case with $Y_2O_3$ 42, 44, 46 or $CeO_2$ 43, 45, 47 as chemical stabilizers.

It could surprisingly be shown that the use of cerium oxide ($CeO_2$) as chemical stabilizer greatly increases the fracture toughness (y axis 40) of the pure material 43 and of the composite material 45, 47. The fracture toughness of the variants according to the invention was determined at the Vickers hardness indentation (HV10). High-strength variants such as pure Ce-stabilized zirconium oxide 43, for example, showed no cracks at the hardness indentation. Therefore, for the high-strength variant a fracture toughness value of 15 $MPa*m^{0.5}$ was assumed by extrapolation in FIG. 4.

Test Series 5: Fracture Toughness as a Function of the Dispersoid Phase

Figure 5:
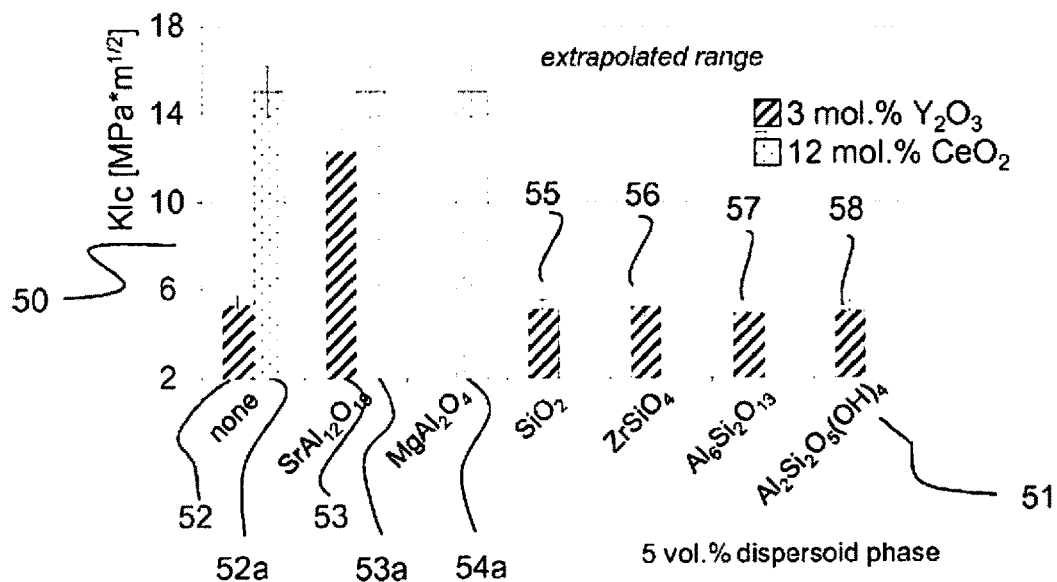
FIG. 5 shows a test series with different dispersoids and their influence on the fracture toughness of the composite material according to the invention.

FIG. 5 shows a test series with different dispersoids and their influence on the fracture toughness (y axis 50) of the composite material according to the invention. The pure zirconium oxide material 52, 52a, zirconium oxide containing strontium hexaaluminate 53, 53a, zirconium oxide containing spinel 54a, zirconium oxide containing quartz 55, zirconium oxide containing zircon 56, zirconium oxide containing mullite 57, and zirconium oxide containing kaolinite 58 as dispersoid phase, partially with $Y_2O_3$ stabilization 52, 53, 55, 56, 57, 58 and partially with $CeO_2$ stabilization 52a, 53a, 54a, are plotted on the x axis 51.

It has surprisingly been shown that the addition of dispersoid phases to the Ce-stabilized composite material had no effect on the fracture toughness.

In contrast, it has surprisingly been shown that the addition of dispersoid phases to the Y-stabilized composite material sometimes had a considerable influence on the fracture toughness. The fracture toughness could be greatly increased from 5.3 to 12.3 MPa*m$^{0.5}$ by adding strontium aluminate (SrAl$_{12}$O$_{19}$) as dispersoid phase to the composite material 53.

Figure 6:
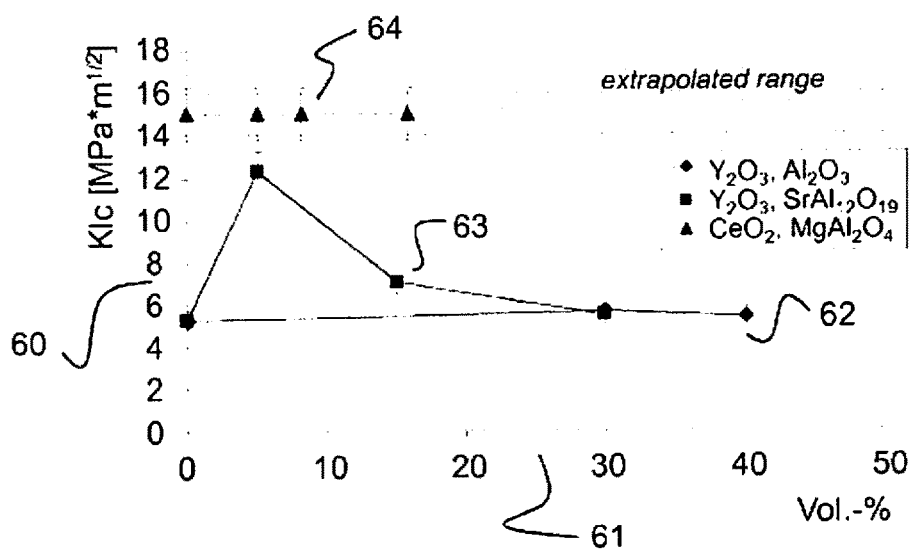
FIG. 6 shows a plurality of test series of the composite material according to the invention with dispersoids and different contents of dispersoid phases.

Test Series 6: Fracture Toughness as a Function of the Content of the Dispersoid Phase FIG. 6 shows a plurality of test series of the composite material according to the invention with dispersoids and different contents of the dispersoid phases. The contents of the dispersoid phase in vol.-% are indicated on the x axis 61. The fracture toughness in MPa*m$^{0.5}$ is plotted on the y axis 60.

Aluminum oxide (Al$_2$O$_3$) 62 and strontium aluminate (SrAl$_{12}$O$_{19}$) 63 in Y-stabilized zirconium oxide, and spinel (MgAl$_2$O$_4$) 64 in Ce-stabilized zirconium oxide were tested. It has surprisingly been shown that, depending on the dispersoid used, with regard to good fracture toughness there is an optimum for the content of the dispersoid phase in the composite material according to the invention. The optimum for strontium aluminate as dispersoid phase in the composite material according to the invention is between 1 and 15 vol.-%

Figure 7:
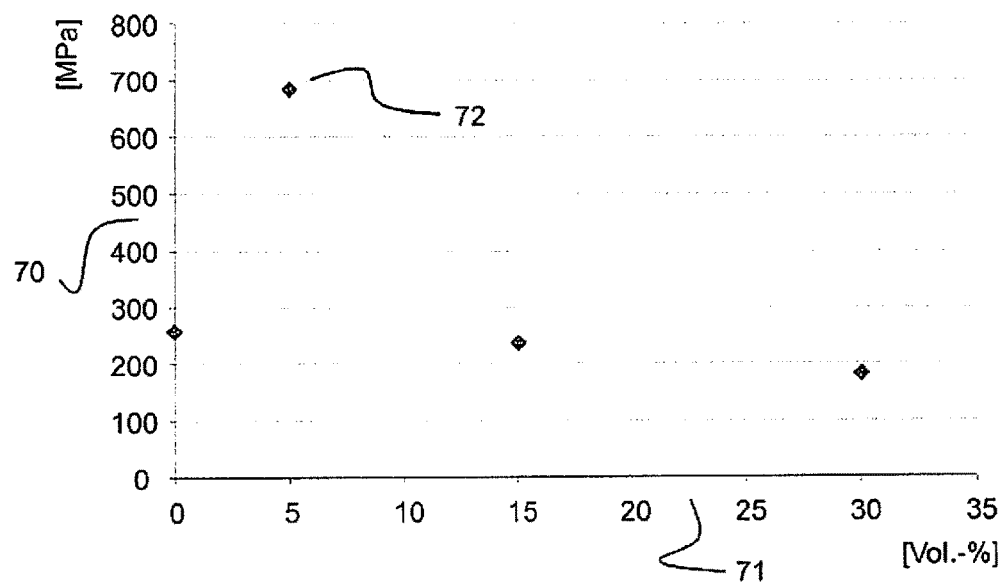
FIG. 7 shows composite materials according to the invention with Y stabilization and strontium hexaaluminate as the secondary phase.

Test Series 7: Damage Tolerance as a Function of the Content of the Dispersoid phase FIG. 7 shows composite materials according to the invention with Y stabilization and strontium hexaaluminate as the secondary phase. The various composite materials are characterized based on their secondary phase contents in vol.-% on the x axis 71. The residual strength of the composite materials following HV50 damage is plotted in MPa on the y axis 70. The tested composite materials are provided with reference numeral 72.

It is clearly shown that for composite materials 72 having a hexaaluminate content between 5 and 15 vol.-%, and in particular with a 5 vol.-% secondary phase, the residual strength of the composite material increases by several times in comparison to the other tested materials.

Figure 8:
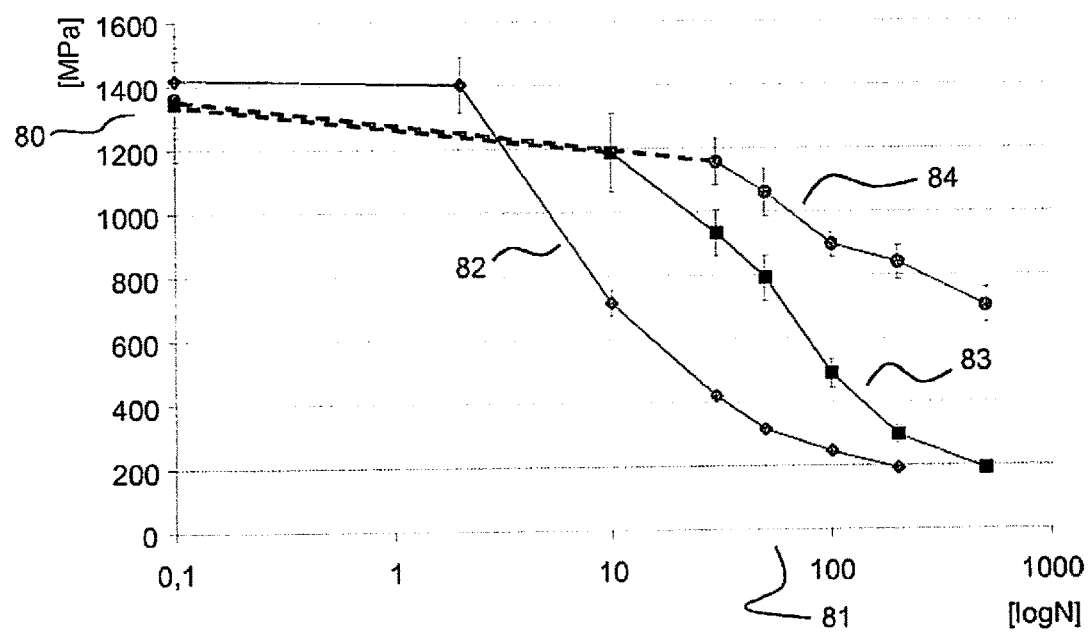
FIG. 8 shows the residual strength values following different damage (in the present case, Vickers hardness indentations) to different material systems, to a zirconia toughened alumina (ZTA) 82, a Y-stabilized polycrystalline zirconia (Y-TZP) 83, and a composite material according to the invention (strontium hexaaluminate-toughened zirconia) 84.

Test Series 8: Damage Tolerance of the Composite Material Compared to Materials of the Prior Art FIG. 8 shows the residual strength values following different damage (in the present case, Vickers hardness indentations) to different material systems, to a zirconia toughened alumina (ZTA) 82, a Y-stabilized polycrystalline zirconia (Y-TZP) 83, and a composite material according to the invention (strontium hexaaluminate-toughened zirconia) 84. The tested indentation load is logarithmically plotted in N on the x axis 81 versus the residual strength in MPa on the y axis 80.

In comparison to materials from the prior art, it is shown that the novel composite material, with the initial strength constant, shows significantly higher damage tolerances following various damage loads.

The advantages of the composite material according to the invention are once again summarized below:

Production of the composite material according to the invention takes place using known, conventional ceramic technology 3-stage sintering (prefiring, HIP, white burning), resulting in greater strength No hydrothermal aging on account of using CeO$_2$ as chemical stabilization Greatly reduced hydrothermal aging due to smaller proportions of Y$_2$O$_3$ as chemical stabilization on account of the mechanical partial stabilization, or the extra addition of other chemical stabilizers which show no negative effect on the aging resistance High damage tolerance Lower-risk hard machining Lesser hardness Use of the composite material according to the invention in the fields of dental technology and dentistry for producing blanks and blocks for CAD/CAM machining in the pre-sintered or dense-sintered state, and for dental prostheses and dental restoration (bridges, crowns, inlays, onlays)

Preferably used as dental root pins, implants, abutments, and other applications Particularly preferably used as spinal implants (spacers/cages, for example)

It is claimed:

1. A composite material comprising:
a ceramic matrix, said ceramic matrix comprising zirconium oxide and at least one secondary phase dispersed therein, wherein the matrix composed of zirconium oxide has a proportion of at least 51 vol.-% of composite material, and wherein the secondary phase has a proportion of from 4 to 6 vol.-% of composite material, wherein 95 to 99% of the zirconium oxide is present in the tetragonal phase based on the total zirconium oxide portion;
wherein the tetragonal phase of the zirconium oxide is stabilized by at least one member selected from the group consisting of chemical stabilization and mechanical stabilization;
wherein the secondary phase comprises at least one member selected from the group consisting of: strontium hexaaluminate, lanthanum aluminate, hydroxyapatite, fluorapatite, tricalcium phosphate, spinel, aluminum oxide, yttrium aluminum garnet, mullite, zircon, quartz, talc, kaolinite, pyrophyllite, potassium feldspar, leucite and lithium metasilicate, and
wherein the chemical stabilization is via addition of a chemical stabilizer selected from the group consisting of Y$_2$O$_3$, CeO$_2$, Gd$_2$O$_3$, Sm$_2$O$_3$, and Er$_2$O$_3$; wherein a total content of chemical stabilizer is <12 mol-% based on a zirconium oxide content.

2. A composite material according to claim 1, wherein the matrix composed of zirconium oxide has an average grain size of 0.1 to 2.0 μm.

3. A composite material according to claim 1, wherein the chemical stabilizer is Y$_2$O$_3$.

4. A composite material according to claim 3, wherein a content of Y$_2$O$_3$ is ≤3 mol, based on the zirconium oxide content.

5. A composite material according to claim 1, wherein at least one of the zirconium oxide or the secondary phase contain a soluble substituent.

6. A composite material according to claim 5, wherein the soluble substituent is selected from the group consisting of Cr, Fe, Mg, Ca, Ti, Y, Ce, a lanthanide and V.

7. A composite material according to claim 6, wherein the soluble substituent is an oxide.

8. A composite material according to claim 1, wherein the secondary phase includes a dispersoid which, due to crystal structure of the dispersoid, allows at least one of shear deformation on the microscopic level or reduces the hardness of the composite material.

9. A composite material according to claim 1, wherein particles of the secondary phase have a particle size of less than or equal to a grain size of the zirconium oxide.

10. A composite material according to claim 1, wherein the particles of the secondary phase have a particle size of from 0.2 to 2.0 μm.

11. A composite material comprising:
a ceramic matrix, said ceramic matrix comprising zirconium oxide and at least one secondary phase dispersed therein, wherein the matrix composed of zirconium oxide has a proportion of at least 51 vol.-% of composite material, and wherein the secondary phase has a proportion of 1 vol.-% of composite material, wherein 90 to 99% of the zirconium oxide is present in the tetragonal phase based on the total zirconium oxide portion; and
wherein the tetragonal phase of the zirconium oxide is stabilized by at least one member selected from the group consisting of chemical stabilization and mechanical stabilization.

12. A composite material according to claim 1, wherein the secondary phase comprises said aluminum oxide.

13. A composite material according to claim 1, wherein the composite material has a hardness<1350.

14. A composite material according to claim 13, wherein the composite material has a hardness of <1200.

15. A composite material according to claim 1, wherein the composite material has a hardness of <1000.

16. A composite material according to claim 1, wherein the composite material has a breaking strength≥800 MPa.

17. A composite material according to claim 1, wherein the damage tolerance or residual strength following an HV50 indentation is >400 MPa.

18. An article of manufacture comprising the composite material of claim 1, wherein the article of manufacture is a member selected from a dental prostheses, a dental restoration, a dental root pin, a dental implant, an abutment and a spinal implant.

19. A method for producing a sintered molded body made of a composite material according to claim 1, comprising the steps of:
a) placing a powder mixture of the ceramic matrix into water,
b) homogenizing in a dissolver;
c) grinding in an agitator ball mill;
d) spray drying to form a granulate;
e) moistening the granulate with water;
f) axially pressing the granulate to form a block;
g) machine cutting a block to form pre-sintered state;
h) sintering the pre-sintered state block to form a sintered block; and
i) hard machining the sintered block.

20. A composite material according to claim 1, wherein the content of $CeO_2$ is ≤12 mol-%, based on the zirconium oxide content.

21. A composite material according to claim 1, wherein the content of $Gd_2O_3$ is ≤3 mol-%, based on the zirconium oxide content.

22. A composite material according to claim 1, wherein the content of $Sm_2O_3$ is ≤3 mol-%, based on the zirconium oxide content.

23. A composite material according to claim 1, wherein the content of $Er_2O_3$ is ≤3 mol-%, based on the zirconium oxide content.

24. A composite material comprising:
a ceramic matrix, said ceramic matrix comprising zirconium oxide and a secondary phase dispersed therein, wherein the matrix composed of zirconium oxide has a proportion of at least 51 vol.-% of composite material, and that the secondary phase has a proportion of from 4 to 6 vol.-% of composite material, wherein 95 to 99% of the zirconium oxide is present in the tetragonal phase based on the total zirconium oxide portion; and
wherein the tetragonal phase of the zirconium oxide is stabilized by at least one member selected from the group consisting of chemical stabilization and mechanical stabilization.

25. A method for producing a sintered molded body made of a composite material according to claim 24, comprising the steps of:
a) placing powder mixture of the zirconium oxide and the secondary phase into water to form an aqueous mixture
b) homogenizing the aqueous mixture in a dissolver to form a homogenized aqueous mixture;
c) grinding the homogenized aqueous mixture in an agitator ball mill to form a ground homogenized aqueous mixture;
d) spray drying to form a granulate;
e) moistening the granulate with water;
f) axially pressing a block;
g) machine cutting a block in a green or pre-sintered state;
h) sintering; and
i) hard machining.

26. A composite material comprising:
a ceramic matrix, said ceramic matrix comprising zirconium oxide and at least one secondary phase dispersed therein, wherein the matrix composed of zirconium oxide has a proportion of at least 51 vol.-% of composite material, and wherein the secondary phase has a proportion of 1 to 10 vol.-% of composite material, wherein 90 to 99% of the zirconium oxide is present in the tetragonal phase based on the total zirconium oxide portion;
wherein the tetragonal phase of the zirconium oxide is stabilized by at least one member selected from the group consisting of chemical stabilization and mechanical stabilization; and
wherein the secondary phase comprises zircon.

* * * * *